United States Patent [19]
Peters et al.

[11] Patent Number: 5,443,445
[45] Date of Patent: Aug. 22, 1995

[54] SURGICAL DEVICE

[75] Inventors: Joseph L. Peters, Ware; James W. Kerr, Gravesend, both of England

[73] Assignee: Clinical Product Development Limited, Gravesend, England

[21] Appl. No.: 129,127

[22] Filed: Oct. 8, 1993

[30] Foreign Application Priority Data

Apr. 8, 1991 [GB] United Kingdom ............... 9107296

[51] Int. Cl.⁶ .................. A61M 1/00; A61M 31/00
[52] U.S. Cl. .................... 604/27; 604/275; 604/278
[58] Field of Search ............ 604/27, 28, 35, 39–45, 604/179, 264, 266, 268, 275, 276, 278, 284, 327, 328, 22; 606/128; 128/DIG. 26

[56] References Cited

U.S. PATENT DOCUMENTS

| | | | |
|---|---|---|---|
| 520,275 | 5/1894 | Sweger | 604/275 |
| 750,276 | 1/1904 | Gruss | 604/39 |
| 1,534,852 | 4/1925 | Hunter | 604/275 |
| 1,602,215 | 10/1926 | Smith | 604/42 |
| 3,771,522 | 11/1973 | Waysilk et al. | 604/28 |
| 3,828,782 | 8/1974 | Polin | 604/328 |
| 3,851,646 | 12/1974 | Sarns | 604/284 |
| 3,908,660 | 9/1975 | Kaplan . | |
| 4,002,170 | 1/1977 | Hansen . | |
| 4,063,557 | 12/1977 | Wuchinich et al. | 604/22 |
| 4,192,294 | 3/1980 | Vasilevsky et al. | 604/22 |
| 4,490,138 | 12/1984 | Lipsky et al. | 604/268 |
| 4,596,554 | 6/1986 | Dastgeer . | |
| 4,645,492 | 2/1987 | Weeks | 604/174 |
| 4,650,473 | 3/1987 | Bartholomew | 604/174 |
| 4,842,583 | 6/1989 | Mailessi | 604/275 |
| 4,870,953 | 10/1989 | DonMichael et al. | 604/22 |
| 4,904,238 | 2/1990 | Williams . | |
| 5,236,414 | 8/1993 | Takasu | 604/22 |

Primary Examiner—C. Fred Rosenbaum
Assistant Examiner—Frank Wilkens, III
Attorney, Agent, or Firm—Watson, Cole, Grindle & Watson

[57] ABSTRACT

An intra-operative colon irrigation system includes a drain tube (1) having a cylindrical body (10) with a forward end formed by a dome-shaped nozzle to prevent intussusception of the bowel into the drain tube. The forward end portion of the body is inserted into the bowel, and a rear end portion has a lug (26) with eyes (27) or securing 'cable straps' (29) which are applied around the body and the collapsed bowel segment downstream of the bowel opening. To assist in breaking up solid faecal masses the drain tube includes an ultrasonic device (16) or other means.

17 Claims, 4 Drawing Sheets

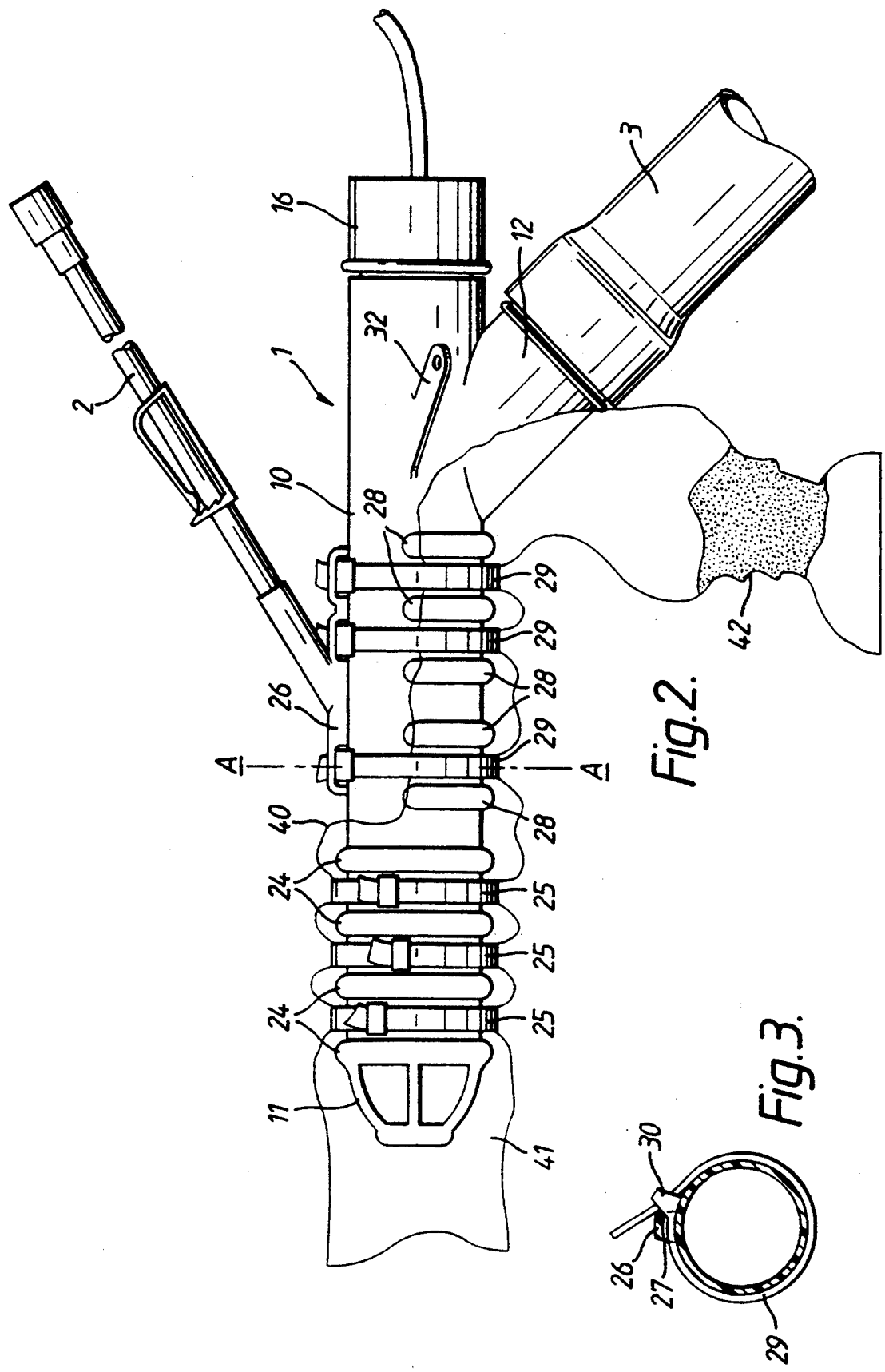

SURGICAL DEVICE

BACKGROUND OF THE INVENTION

This invention relates to surgical devices, and in particular to a device for use in cleansing the colon in the course of surgical procedures.

It has become usual practice when performing certain surgical operations, such as to remove a growth obstructing the bowel, to cleanse the colon upstream of the obstruction by irrigating it with a suitable washing liquid, for example saline solution, to remove residual faecal matter. A rigid draining or discharge tube is partially inserted into a lateral opening made in the bowel and is secured in place by ligatures applied around the bowel over the end portion of the tube inserted into the bowel. A length of flexible tubing is connected to the outer end of the tube for conducting the washing liquid and faeces to an appropriate receptacle. The cleansing can be carried out in a continuous manner, in which case cleansing solution is introduced into the bowel at a suitable upstream location, e.g. near the appendix and is allowed to stream through the intestine to the discharge tube. Alternatively, the cleansing may be performed in a batchwise sense by delivering a volume of cleansing solution into the bowel, causing it to swill around within the bowel and then allowing it to drain out through the discharge tube. For the purpose of introducing the washing solution it is known for the drain tube to be equipped with a lateral branch connector for attachment of a tube through which the liquid is poured into the bowel.

The known intra-operative colon irrigation systems are satisfactory, but they are not without limitations and drawbacks. It is difficult to secure the drain tube reliably within the bowel, and if it is not connected securely, it can become detached, with the result that the washing liquid, etc., may spill out of the bowel in an uncontrolled manner. In addition, as the drain tube substantially fills the inner cross-section of the bowel, it presents an open end of large area into which the bowel wall has a tendency to enter, causing trauma by intussusception of the bowel. While the cleansing is effective when the faeces within the bowel are fluid, it is not so efficacious when a solid faecal mass is present.

SUMMARY OF THE INVENTION

The present invention addresses these drawbacks, and in accordance with a first aspect of the invention there is provided a drain tube for an intra-operative colon irrigation system having a forward end for insertion into the bowel and screen means extending across the forward end opening of the tube to prevent intussusception of the bowel into the tube.

In a preferred embodiment the screen means is integral with the tube and has the general form of a dome-shaped nozzle projecting forwardly from the end of the tube and defining inlet holes of relatively large area and few, e.g. 3 to 7 in number. The nozzle may comprise a central ring coaxial with the tube and having an inner diameter approximately half that of the tube, and radial spokes, e.g. four spokes uniformly spaced apart around the ring, connecting the ring to the end of the tube.

According to a second aspect of the invention there is provided a drain tube for an intra-operative colon irrigation system, comprising a forward end portion for insertion into the bowel, a rear end portion to remain outside the bowel, and means fixed to the exterior of the rear end portion for secure connection thereto of at least one tie element to be tightened around the tube for clamping thereto a segment of bowel downstream of the bowel opening through which the forward end portion of the tube is inserted.

The tie elements preferably comprise plastics straps, commonly referred to as "cable straps", which have a long tail with serrations therealong and an integral locking device at one end of the tail and through which the free end of the tail can be inserted to form a loop. The tail can be moved freely through the locking device to reduce the size of the loop, but is securely locked against movement in the opposite direction to prevent expansion of the loop and hence loosening of the strap after it has been tightened around the drain tube and bowel segment.

The means fixed to the exterior of the tube conveniently comprises an integral lug with an eye through which the strap may be passed, and it is preferable for a plurality of such means to be provided and to be spaced apart along the tube for cooperation with respective straps.

By provision of the fixing means fast with the tube a reliable attachment of the drain tube to the colon can be ensured whereby their accidental detachment is prevented.

According to a third aspect the invention resides in a drain tube for an intra-operative colon irrigation system, wherein a device incorporated within the tube is operable to assist in breaking-up solid faecal masses and homogenising the faecal matter.

The device may be an ultrasonic device, a device for injecting fluid under pressure, or a mechanical device, e.g., having rotating blades or vanes, which could be driven electrically or by pressurised fluid. The device preferably as an effective part located substantially at the forward end of tubular body, i.e., with a distance of about 2 cms from the forward end.

In a preferred construction an ultrasonic device is provided and comprises a probe arranged to extend axially and substantially along the entire length of the drain tube.

A better understanding of the invention and its novel features will be gained from the following detailed description which is given by way of example and with reference to the accompanying drawings.

BRIEF DESCRIPTION OF THE DRAWINGS

FIG. 2 is a side elevation illustrating the drainage tube applied to a bowel;

FIG. 3 is a section taken along the line 3—3 of FIG. 2;

DETAILED DESCRIPTION OF THE PREFERRED EMBODIMENTS

Figure 1:
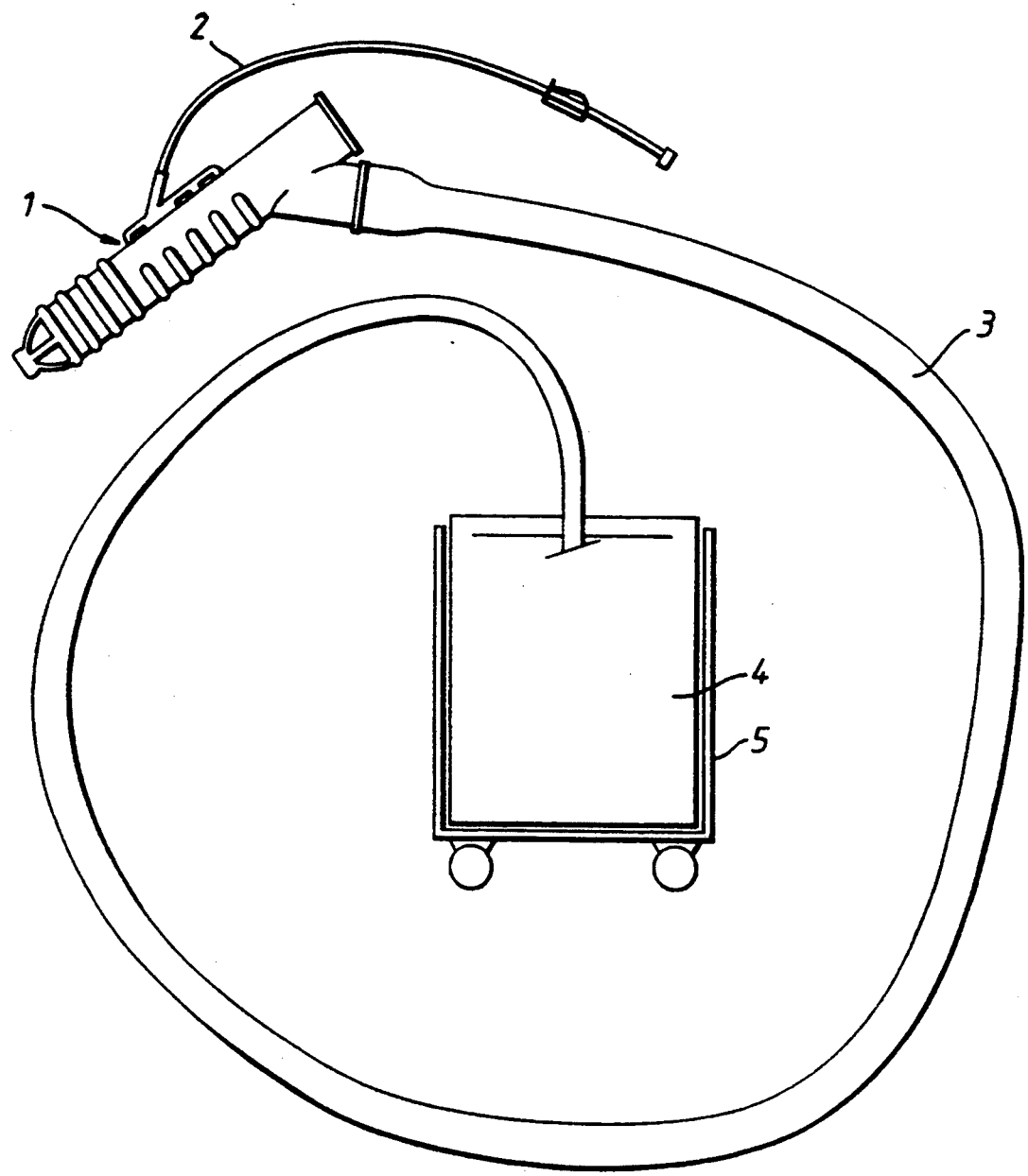
FIG. 1 illustrates an intra-operative colon irrigation system incorporating a drainage tube embodying the invention.

The intra-operative colon irrigation system shown in FIG. 1 comprises a drain tube 1, described more closely below, having a branch connection to which is attached a flexible tubing 2 for connection to a supply of cleansing solution, and a flexible tube 3 connected to the outlet port of the drain tube 1 and leading to a receptacle which, as shown, comprises a bag 4 having an inlet possibly equipped with a non-return valve and preferably positioned in a wheeled container 5.

The drain tube 1 is of unitary moulded construction and comprises a cylindrical body 10 with a dome-shaped nozzle 11 defining a screen covering the opening at the forward end of the body, an axially inclined branch tube 12 of essentially the same diameter as the body connected to a rear end portion of the body and forming a handle and a union for attachment of the flexible tube 3, and an axially inclined inlet tube 14 connected to a medial portion of the body and to which the wash liquid supply tube 2 is connected.

Figure 6:
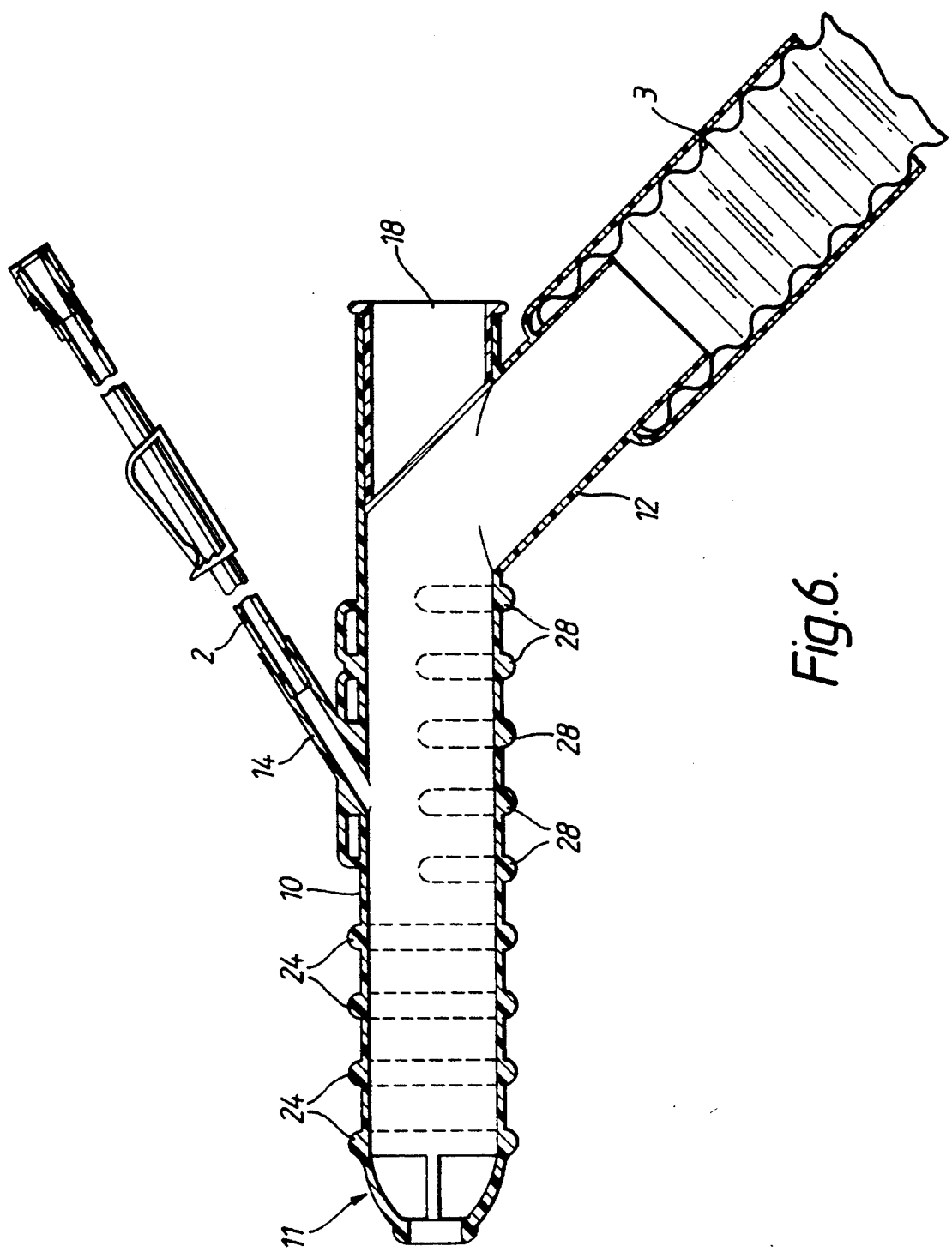
FIG. 6 is a view corresponding to FIG. 4, but with the ultrasonic device replaced by a plug.

A modification is illustrated in FIG. 6 according to which the tube 12 defines a spigot to receive the end of the tube 3, and is formed with an integral sheath which encloses a significant length of the tube 3 to provide an extended handle allowing the drain tube to be gripped without having to touch the tube 3.

Figures 4, 5:
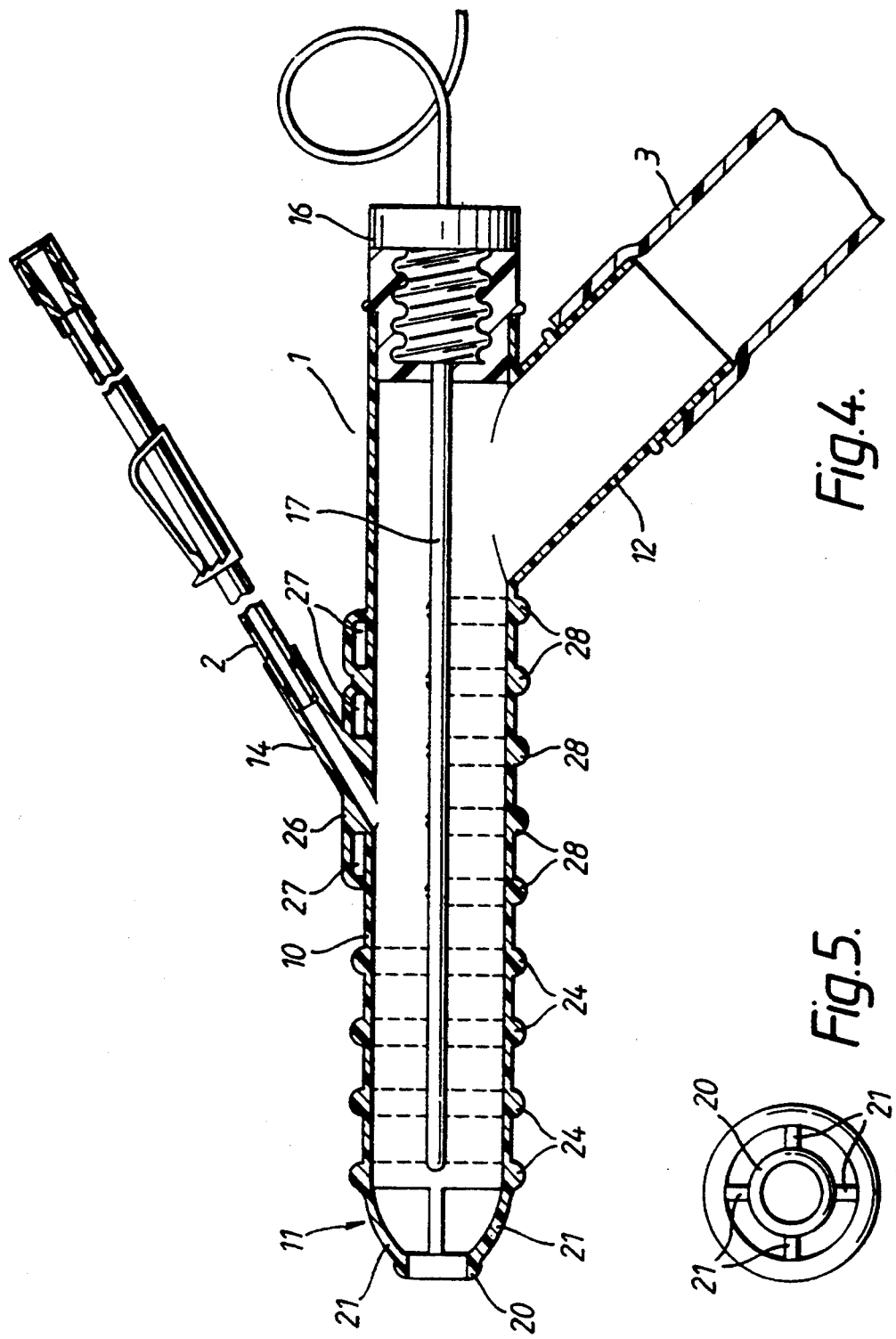
FIG. 4 is an axial cross-section through the drain tube.
FIG. 5 is a front elevation of the nozzle at the front end of the drain tube.

As shown in FIGS. 2 and 4 an ultrasonic device 16 is fitted to the rear end of the body 10 and has a probe 17 which extends axially along its bore for substantially the entire length of the body. The ultrasonic device is optional and as shown in FIG. 6 the drain tube is fitted with a plug 18 in place of the ultrasonic device. Other types of device may be provided instead of the device 16 for breaking up faecal masses, such as by injecting water or air under pressure. If the facility of including the device 16 is not required, the branch tube 12 can be omitted with the flexible tube 3 then be connected to the rear end of the cylindrical body 10.

The nozzle 11 is shown to comprise a central ring 20, coaxial with the body and having an inner diameter approximately half that of body 10, and four curved spokes 21 connecting the ring to the end of the body 10. The nozzle thereby defines five openings of relatively large area for washing solution and faecal matter to enter the drain tube, yet the nozzle forms a support structure to preclude intussusception of the bowel into the drain tube. The described nozzle is the preferred form, but other configurations are obviously possible within the scope of the invention.

Four axially spaced annular collars 24 extend around the exterior of the body 10 at the forward end portion of the drain tube intended to be inserted into the bowel, and serve to locate and cooperate with securing straps 25 applied around the bowel and the forward end portion of the drain tube located therein. At a medial portion and conveniently in longitudinal alignment with the tube 4, the body 10 is provided with an upstanding lug or ridge 26 in which axially spaced holes or eyes 27 are formed. On the side of the body opposite the lug 26 semi-annular collars 28 are provided and define between them grooves in circumferential alignment with the respective eyes 27 for cooperation with further straps 29 which are passed through the eyes 28, as shown in FIGS. 2 and 3. The straps 25, 29 are of a known and commercially available form frequently used and known as "cable straps". They have an elongate tail with serrations along its length, and a locking device 30 at one end of the tail. The free end of the tail is inserted through the locking device to form the strap into a loop and can be moved freely through the device to reduce the size of the loop. The locking device prevents reverse movement of the tail in a direction to expand the loop. Of course the invention is not limited to use of this form of strap and other securing elements such as ligatures could be used instead. Similarly, it is not essential for the collars 24, 28 to be as described and any form of protrusions which will define recesses to locate the straps 25, 29 and prevent the drain tube slipping out of the bowel will be satisfactory.

In use of the drain tube 1, an incision 40 is made in the wall of the bowel 41, e.g. a short distance upstream of an obstruction 42 to be removed, and the forward end portion of drain tube 1 is inserted through the bowel opening thus formed to extend in an upstream direction. The ring 20 of the nozzle forms a nose which can assist insertion of the drain tube into the bowel. Securing straps 25 are applied around the bowel 41 and the inserted forward end portion of the drain tube 1. The further straps 29 are also applied, each being passed through a respective eye 27 and around the body 10 and the segment of intestine immediately downstream of the incision 40. This bowel segment is collapsed upon itself and clamped against the body 10 by the straps 29 which, in conjunction with the eyes 27 and collars 28, ensure the drain tube is held securely connected to the bowel 40.

A volume of cleansing solution can be introduced in the section of bowel to be cleansed by means of the tube 2, the tube 3 being pinched closed to prevent the liquid being discharged prematurely. After rinsing the bowel with the liquid it is allowed to drain into the container 4 via the drain tube 1 and flexible tube 3. If on the other hand cleansing solution is to be flushed through the bowel from an upstream location, the end of the tube 2 is closed off by a cap and liquid is allowed to drain continuously through the drain tube. Intussusception of the bowel into the drain tube is prevented by the nozzle 11, the openings of which are still large enough not to impede flow from the bowel into the drain tube.

If a solid faecal mass is encountered the ultrasonic probe 16, 17 maybe energised to assist in breaking up the mass to allow it to be washed out of the bowel. It has been found most effective in homogenising the faecal matter if the operative part, i.e., the tip of the probe, is located at the forward end of the body 10 immediately behind the nozzle 11.

In order to avoid risk of the drain tube being pulled out from the abdominal wound under the weight of the tube 3 and its contents, the drain tube may be secured by stitching to the skin of the patient, for which purpose the body may be provided with an integral wing 32 with a hole through which the thread can be passed.

We claim:

1. A drain tube for an intra-operative colon irrigation system, comprising a tubular body with a forward end portion for insertion into the bowel, screen means forming a dome-shaped nozzle at the forward end of the tubular body for preventing intussusception of the bowel into the tubular body, (10) the nozzle having several forwardly directed holes and including a ring defining a central hole and a plurality of spokes extending outwardly and rearwardly from the ring to separate a plurality of further holes spaced around the central hole.

2. A drain tube as claimed in claim 1, wherein the screen includes approximately 3 to 7 holes of relatively large area.

3. A drain tube as claimed in claim 1, wherein the screen means is integral with the tubular body.

4. A drain tube as claimed in claim 1, wherein the tubular body includes a rear end portion to remain outside of the bowel, and a lug fixed to the exterior of the rear end portion and defining an eye for secure connection of at least one tie element to be tightened around the tubular body for clamping thereto a segment of bowel downstream of the bowel opening through which the forward end portion of the tubular body is inserted.

5. A drain tube as claimed in claim 1, including a device operable to facilitate break up of solid faecal masses extending into the tubular body.

6. A drain tube as claimed in claim 5, wherein the device has an effective part located substantially at the forward end of the tubular body.

7. A drain tube as claimed in claim 5, wherein the device is an ultra-sonic device.

8. A drain tube as claimed in claim 7, wherein the ultra-sonic device comprises a probe extending axially substantially along the length of the tubular body.

9. A drain tube as claimed in claim 5, wherein the tubular body has a discharge outlet arranged to define a handle for holding the drain tube.

10. A drain tube for an intra-operative colon irrigation system, comprising a tubular body with a forward end portion for insertion into a bowel, a rear end portion to remain outside of the bowel, and a lug fixed to the exterior of the rear end portion and defining an eye for secure connection of at least one tie element to be tightened around the tubular body for clamping thereto a segment of bowel downstream of the bowel opening through which the forward end portion of the tubular body is inserted.

11. A drain tube as claimed in claim 10, wherein a plurality of eyes are provided for securing respective tie elements at positions spaced apart along the tubular body.

12. A drain tube as claimed in claim 10, wherein the tubular body (28) has means (28) defining a recess about the circumference of the tubular body for location of the tie element and the bowel clamped thereby.

13. A drain tube as claimed in claim 10, wherein the forward end portion of the tubular body comprises means defining at least one recess about the tubular body for location of a tie element extending about the forward end portion of the tubular body and the bowel segment in which said forward end portion is inserted.

14. A drain tube as claimed in claim 10, including a tie element comprising a strap with an elongate tail for insertion through the eye and locking means for receiving the free end of the tail to form the strap into a loop, the locking means permitting movement of the tail to reduce the size of the loop but preventing reverse movement to expand the loop.

15. A drain tube as claimed in claim 10, wherein the tubular body comprises a branch connection for delivery of cleansing solution to the interior of the tubular body.

16. A drain tube as claimed in claim 10, wherein means are provided on the tubular body to facilitate attachment of the drain tube to the skin of the patient by stitching.

17. A drain tube as claimed in claim 10, wherein the rear end portion of the tubular body defines an axially inclined discharge outlet and an axial port, and including a device operable to assist in breaking up solid faecal masses located in the axial port.

* * * * *